US009551640B2

(12) United States Patent
Lam et al.

(10) Patent No.: US 9,551,640 B2
(45) Date of Patent: *Jan. 24, 2017

(54) WIRE-PULL TEST LOCATION IDENTIFICATION ON A WIRE OF A MICROELECTRONIC PACKAGE

(71) Applicant: International Business Machines Corporation, Armonk, NY (US)

(72) Inventors: Mark T. W. Lam, Singapore (SG); Katsuyuki Yonehara, Kanagawa-ken (JP)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/844,071

(22) Filed: Sep. 3, 2015

(65) Prior Publication Data

US 2015/0377611 A1 Dec. 31, 2015

Related U.S. Application Data

(63) Continuation of application No. 14/093,841, filed on Dec. 2, 2013, now Pat. No. 9,255,867.

(51) Int. Cl.
*G01L 1/24* (2006.01)
*G01N 3/08* (2006.01)
(Continued)

(52) U.S. Cl.
CPC ............... *G01N 3/08* (2013.01); *G01B 11/14* (2013.01); *G01N 3/068* (2013.01); *H01L 24/78* (2013.01);
(Continued)

(58) Field of Classification Search
CPC .... G01N 3/08; G01N 3/068; G01N 2203/028; G01B 11/14; H01L 24/49
(Continued)

(56) References Cited

U.S. PATENT DOCUMENTS 4,282,759 A 8/1981 Merrell
4,453,414 A 6/1984 Ronemus et al.
(Continued)

FOREIGN PATENT DOCUMENTS

EP 1333263 B1 11/2006

OTHER PUBLICATIONS

U.S. Appl. No. 14/093,841, 1 page.
(Continued)

*Primary Examiner* — Max Noori
(74) *Attorney, Agent, or Firm* — Francis Lammes; Stephen J. Walder, Jr.; Damion C. Josephs

(57) ABSTRACT

A mechanism is provided for identifying a wire-pull test location on a wire of a microelectronic package. A first distance between a first terminating location of the wire on the microelectronic package and a second terminating location of the wire on the microelectronic package is determined. Based on the first distance, a second distance from either the first terminating location or the second terminating location is determined as the wire-pull test location for testing a strength of a connection of the wire to at least one of the first terminating location or the second terminating location. An adjustment is performed such that a visual guide is oriented on the wire at the wire-pull test location.

13 Claims, 5 Drawing Sheets

(51) Int. Cl.
*G01N 3/06* (2006.01)
*G01B 11/14* (2006.01)
*H01L 23/00* (2006.01)

(52) U.S. Cl.
CPC ............ *G01N 2203/0041* (2013.01); *G01N 2203/0067* (2013.01); *G01N 2203/028* (2013.01); *G01N 2203/0296* (2013.01); *G01N 2203/0647* (2013.01); *H01L 24/48* (2013.01); *H01L 24/49* (2013.01); *H01L 2224/48465* (2013.01); *H01L 2224/49171* (2013.01); *H01L 2224/789* (2013.01); *H01L 2224/78753* (2013.01); *H01L 2224/859* (2013.01); *H01L 2924/00014* (2013.01)

(58) Field of Classification Search
USPC .......................... 73/827, 800; 702/43, 35–36
See application file for complete search history.

(56) References Cited

U.S. PATENT DOCUMENTS

| | | | |
|---|---|---|---|
| 4,757,315 A * | 7/1988 | Lichtenberg | G01S 13/84 342/125 |
| 4,794,800 A | 1/1989 | Atkinson | |
| 4,895,028 A * | 1/1990 | Mayer | G01N 3/08 73/827 |
| 4,907,458 A | 3/1990 | Biggs | |
| 5,275,058 A | 1/1994 | Pham et al. | |
| 5,591,920 A | 1/1997 | Price et al. | |
| 5,686,670 A | 11/1997 | Vanderlip | |
| 6,758,385 B2 | 7/2004 | Farassat | |
| 2003/0146263 A1 | 8/2003 | Farassat | |
| 2011/0199737 A1* | 8/2011 | Yonehara | H01L 23/13 361/728 |
| 2014/0370663 A1* | 12/2014 | Bayerer | H01L 21/52 438/125 |
| 2015/0153261 A1* | 6/2015 | Lam | G01N 3/08 702/43 |

OTHER PUBLICATIONS

"Wire Pull", Nordson Corporation, http://www.nordson.com/en-us/divisions/dage/solutions/testtypes/Pages/WirePull.aspx, retrieved Sep. 9, 2013, 1 page.

Wang, Caiyuan et al., "The Quality Test of Wire Bonding", Modern Applied Science, CCSE, vol. 3, No. 12, Dec. 2009, pp. 50-56.

* cited by examiner

US 9,551,640 B2

WIRE-PULL TEST LOCATION IDENTIFICATION ON A WIRE OF A MICROELECTRONIC PACKAGE

BACKGROUND

The present application relates generally to an improved data processing apparatus and method and more specifically to mechanisms for identifying a wire-pull test location on a wire of a microelectronic package.

Wire-pull is a long established technique for testing the integrity of wire-bond interconnects within microelectronic packages. The principle behind basic wire-bond testing is positioning of a hook underneath the wire and pulling in a Z-axis either until the bond breaks (destructive testing) or a predefined force is reached (non-destructive testing). Wire bond testing is covered by the external standard MIL-STD-883 (Methods 2011.7 for destructive testing and 2023.5 for non-destructive).

SUMMARY

In one illustrative embodiment, a method, in a data processing system, is provided for identifying a wire-pull test location on a wire of a microelectronic package. The illustrative embodiment determines a first distance between a first terminating location of the wire on the microelectronic package and a second terminating location of the wire on the microelectronic package. Based on the first distance, the illustrative embodiment determines a second distance from either the first terminating location or the second terminating location as the wire-pull test location for testing a strength of a connection of the wire to at least one of the first terminating location or the second terminating location. The illustrative embodiment then performs an adjustment such that a visual guide is oriented on the wire at the wire-pull test location.

In other illustrative embodiments, a computer program product comprising a computer useable or readable medium having a computer readable program is provided. The computer readable program, when executed on a computing device, causes the computing device to perform various ones of, and combinations of the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE SEVERAL VIEWS OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Again, wire-pull is along established technique for testing the integrity of wire-bond interconnects within microelectronic packages. Wire-pull readings are important for the wire-bonding process, because the wire-pull readings have a direct impact on whether a microelectronic package is deemed functional. Hence, the position or location of the actual wire-pull may determine whether the wire-bond interconnect is stable or good. In the microelectronic industry, the location of the wire-pull is usually defined but not accurately pulled as the wire-pull is performed through human estimation and, thus, subject to human error.

Thus, the illustrative embodiments provide for identifying a wire-pull test location on a wire of a microelectronic package by projecting a visual guide at an optimal wire-pull test location on the microelectronic package. In order to determine the wire-pull test location, a first distance is determined between a first terminating location of the wire on the microelectronic package and a second terminating location of the wire on the microelectronic package. Based on the first distance, a second distance is determined from the first terminating location or the second terminating location as the optimal wire-pull test location for testing a strength of a connection of the wire to at least one of the first terminating location or the second terminating location. An adjustment is then made so that the visual guide is oriented on the wire at the wire-pull test location.

Figure 1:
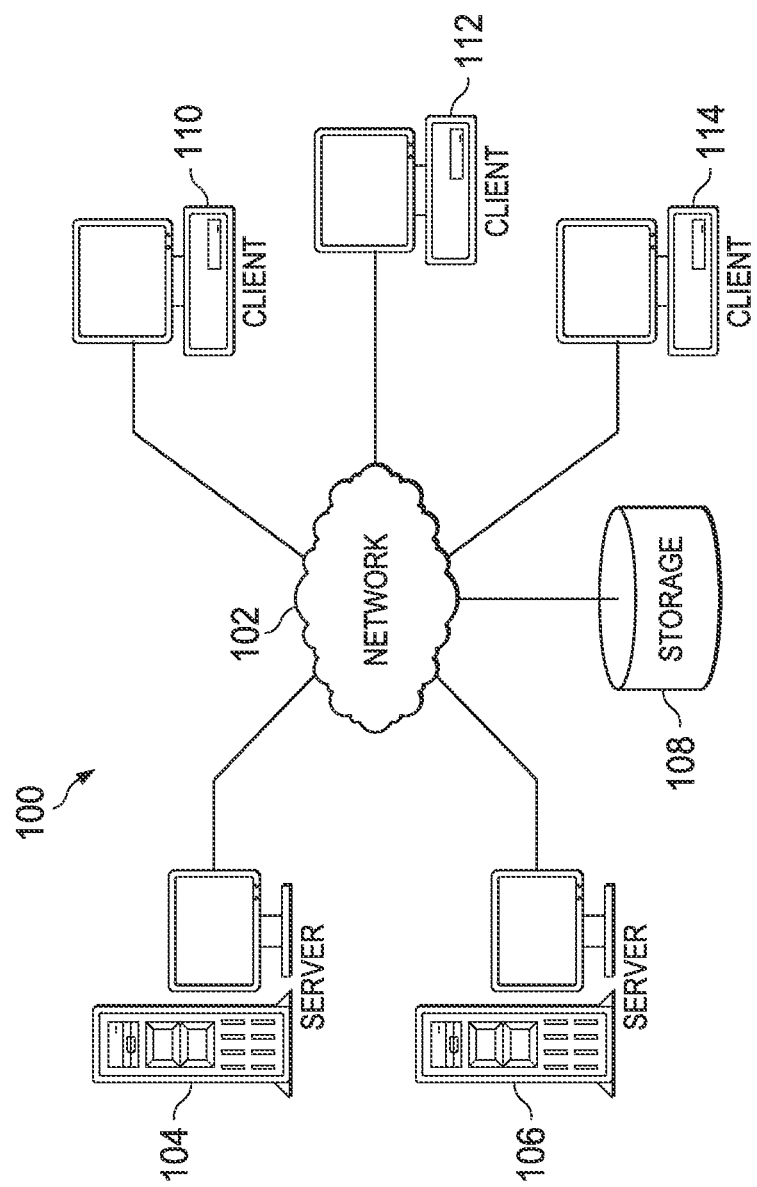
FIG. 1 is an example diagram of a distributed data processing system in which aspects of the illustrative embodiments may be implemented.
Figure 2:
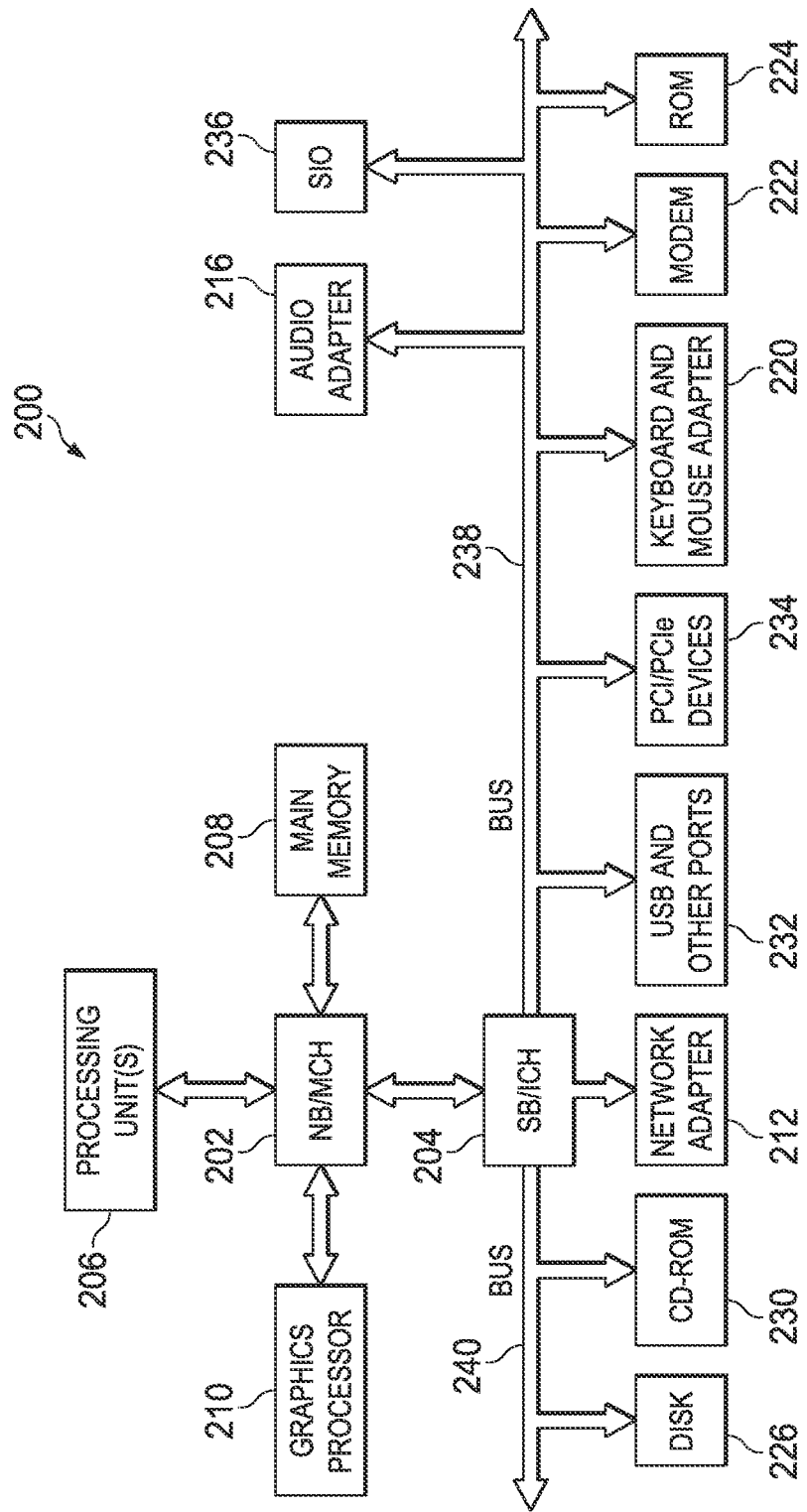
FIG. 2 is an example block diagram of a computing device in which aspects of the illustrative embodiments may be implemented.

Thus, the illustrative embodiments may be utilized in many different types of data processing environments. In order to provide a context for the description of the specific elements and functionality of the illustrative embodiments, FIGS. 1 and 2 are provided hereafter as example environments in which aspects of the illustrative embodiments may be implemented. It should be appreciated that FIGS. 1 and 2 are only examples and are not intended to assert or imply any limitation with regard to the environments in which aspects or embodiments of the present invention may be implemented. Many modifications to the depicted environments may be made without departing from the spirit and scope of the present invention.

FIG. 1 depicts a pictorial representation of an example distributed data processing system in which aspects of the illustrative embodiments may be implemented. Distributed data processing system 100 may include a network of computers in which aspects of the illustrative embodiments may be implemented. The distributed data processing system 100 contains at least one network 102, which is the medium used to provide communication links between various devices and computers connected together within distributed data processing system 100. The network 102 may include connections, such as wire, wireless communication links, or fiber optic cables.

In the depicted example, server 104 and server 106 are connected to network 102 along with storage unit 108. In addition, clients 110, 112, and 114 are also connected to network 102. These clients 110, 112, and 114 may be, for example, personal computers, network computers, or the like. In the depicted example, server 104 provides data, such as boot files, operating system images, and applications to the clients 110, 112, and 114. Clients 110, 112, and 114 are clients to server 104 in the depicted example. Distributed data processing system 100 may include additional servers, clients, and other devices not shown.

In the depicted example, distributed data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational, and other computer systems that route data and messages. Of course, the distributed data processing system 100 may also be implemented to include a number of different types of networks, such as for example, an intranet, a local area network (LAN), a wide area network (WAN), or the like. As stated above, FIG. 1 is intended as an example, not as an architectural limitation for different embodiments of the present invention, and therefore, the particular elements shown in FIG. 1 should not be considered limiting with regard to the environments in which the illustrative embodiments of the present invention may be implemented.

FIG. 2 is a block diagram of an example data processing system in which aspects of the illustrative embodiments may be implemented. Data processing system 200 is an example of a computer, such as client 110 in FIG. 1, in which computer usable code or instructions implementing the processes for illustrative embodiments of the present invention may be located.

In the depicted example, data processing system 200 employs a hub architecture including north bridge and memory controller hub (NB/MCH) 202 and south bridge and input/output (I/O) controller hub (SB/ICH) 204. Processing unit 206, main memory 208, and graphics processor 210 are connected to NB/MCH 202. Graphics processor 210 may be connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, white PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 may be connected to SB/ICH 204.

An operating system runs on processing unit 206. The operating system coordinates and provides control of various components within the data processing system 200 in FIG. 2. As a client, the operating system may be a commercially available operating system such as Microsoft® Windows 7®. An object-oriented programming system, such as the Java™ programming system, may run in conjunction with the operating system and provides calls to the operating system from Java™ programs or applications executing on data processing system 200.

As a server, data processing system 200 may be for example, an IBM® eServer™ System P® computer system, running the Advanced Interactive Executive operating system or the LINUX® operating system. Data processing system 200 may be a symmetric multiprocessor (SNIP) system including a plurality of processors in processing unit 206. Alternatively, a single processor system may be employed.

Instructions for the operating system, the object-oriented programming system, and applications or programs are located on storage devices, such as HDD 226, and may be loaded into main memory 208 for execution by processing unit 206. The processes for illustrative embodiments of the present invention may be performed by processing unit 206 using computer usable program code, which may be located in a memory such as, for example, main memory 208, ROM 224, or in one or more peripheral devices 226 and 230, for example.

A bus system, such as bus 238 or bus 240 as shown in FIG. 2, may be comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, may include one or more devices used to transmit and receive data. A memory may be, for example, main memory 208, ROM 224, or a cache such as found in NB/MCH 202 in FIG. 2.

Those of ordinary skill in the art will appreciate that the hardware in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

Figure 3:
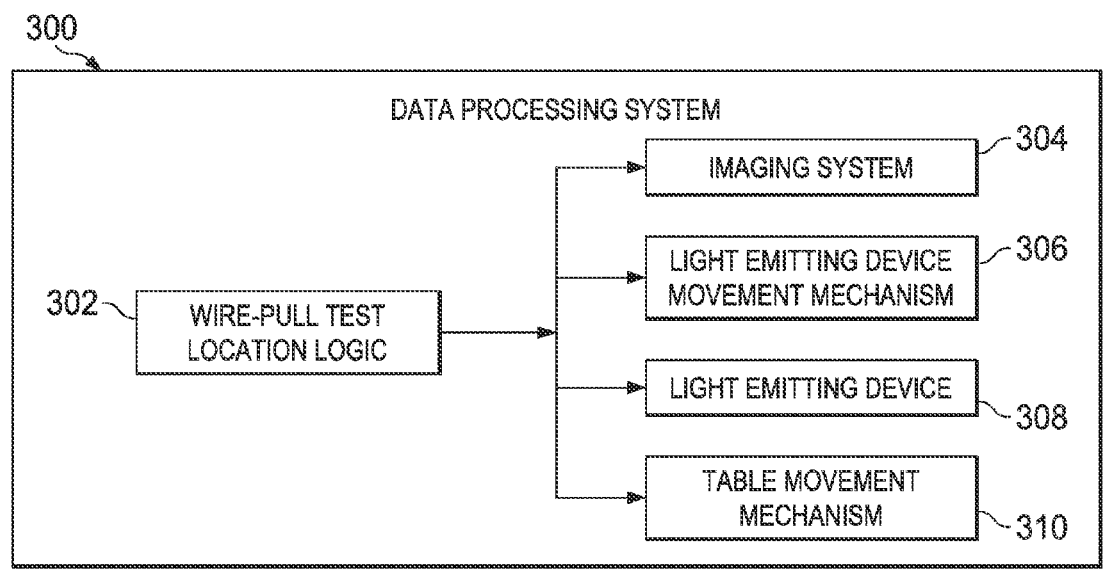
FIG. 3 depicts a data processing system for identifying a wire-pull test location on a wire of a microelectronic package in accordance with an illustrative embodiment.

FIG. 3 depicts a data processing system for identifying a wire-pull test location on a wire of a microelectronic package in accordance with an illustrative embodiment. Data processing system 300 comprises wire-pull test location logic 302 coupled to imaging system 304, light emitting device movement mechanism 306, light emitting device 308, and table movement mechanism 310. With a microelectronic package resting upon a table, wire-pull test location logic 302 initializes imaging system 304 to capture an image of the microelectronic package, which comprises a plurality of components fixed to a substrate where a first subset of the plurality of components are coupled to a second subset of the plurality of components via a set of terminators and a set of wires. Imaging system 304 may be a digital imaging system, an optical imaging system through a scope, or the like.

With an image of the microelectronic package, wire-pull test location logic 302 determines a first distance between a first terminating location of a wire on the microelectronic package and a second terminating location of the same wire on the microelectronic package. Based on the first distance, wire-pull test location logic 302 determines a second distance from either the first terminating location or the second terminating location as the wire-pull test location for testing a strength of a connection of the wire to at least one of the first terminating location or the second terminating location. The wire-pull test location is a predetermined distance such as one-third, one-fourth, one-fifth, or the like, of the first distance and could be measured from the first terminating location or second terminating location.

With the wire-pull test location identified, wire-pull test location logic 302 initializes light emitting device 308 such that a visual guide is displayed on the microelectronic package. The visual guide may be a reflection by the wire of a beam of light that is emitted from a light emitting device, which may be a light emitting diode (LED), a light bulb, or a laser, or the like. Light emitting device 308 may be at an angle to the table and the microelectronic package that is an angle other than perpendicular so that the beam of light is reflected by the wire at the wire-pull test location without being blocked by a user performing a wire-pull test at the wire-pull test location. However, light emitting device 308 may be at a perpendicular angle to the table and the microelectronic package so that the beam of light is reflected by the wire at the wire-pull test location without being blocked by a user performing a wire-pull test at the wire-pull test location.

Using images from imaging system 304, wire-pull test location logic 302 may signal one or both of tight emitting device movement mechanism 306 or table movement mechanism 310, such that one or both of light emitting device movement mechanism 306 or table movement mechanism 310 make an adjustment so that the visual guide is oriented on the wire at the wire-pull test location. In one embodiment, the adjustments may comprise light emitting device movement mechanism 306 adjusting a configuration of light emitting device 308 providing the visual guide, where table movement mechanism 310 makes no movements to the table upon which the microelectronic package rests and light emitting device movement mechanism 306 automatically adjusts light emitting device 308 so that the visual guide appears on the wire at the wire-pull test location.

In another embodiment, the adjustments may comprise table movement mechanism 310 adjusting a configuration of the table upon which the microelectronic package rests, where light emitting device movement mechanism 306 makes no movement to light emitting device 308 providing the visual guide and table movement mechanism 310 automatically adjusts the table so that the visual guide emitted by the light emitting device appears on the wire at the wire-pull test location. In yet another embodiment, the adjustments may comprise adjustments made by both light emitting device movement mechanism 306 and table movement mechanism 310 so that tight emitting device movement mechanism 306 automatically adjusts light emitting device 308 and table movement mechanism 310 automatically adjusts the table upon which the microelectronic package rests so that the visual guide emitted by the light emitting device appears on the wire at the wire-pull test location.

In still another embodiment, wire-pull test location logic 302 may provide visual indicators to a user of data processing system 300 so that, if either or both of light emitting device 308 or the table upon which the microelectronic package rests cannot be adjusted automatically, the user can adjust a configuration of at least one of light emitting device 308 or the table upon which the microelectronic package rests so that the visual guide emitted by the light emitting device appears on the wire at the wire-pull test location as per an indication of the movement of the at least one of light emitting device 308 or the table to the user via the visual indicators.

Figure 4:
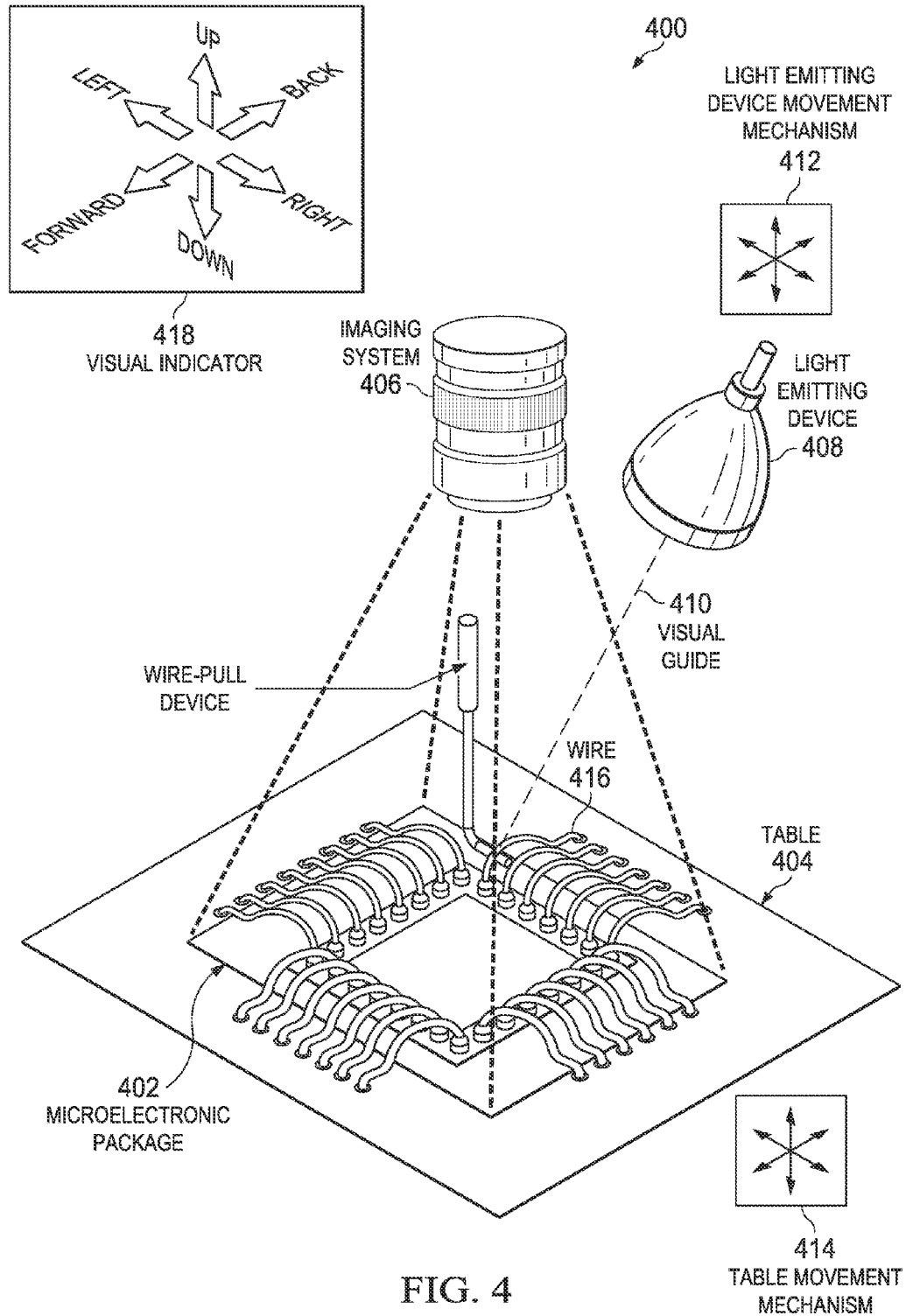
FIG. 4 depicts an exemplary wire-pull environment in accordance with an illustrative embodiment.

FIG. 4 depicts an exemplary wire-pull environment in accordance with an illustrative embodiment. As is illustrated in wire-pull environment 400, microelectronic package 402 rests upon table 404. Once wire-pull test location logic, such as wire-pull test location logic 302 from FIG. 3, initializes, imaging system 406 captures an image of the microelectronic package. The wire-pull test location logic utilizes this image to determine the wire-pull test location for testing a strength of a connection of the wire to at least one of the first terminating location or the second terminating location. With the wire-pull test location identified, the wire-pull test location logic initializes light emitting device 408 such that visual guide 410 is displayed on the microelectronic package.

Using additional images from imaging system 406, the wire-pull test location logic may signal one or both of light emitting device movement mechanism 412 or table movement mechanism 414, such that one or both of tight emitting device movement mechanism 412 or table movement mechanism 414 make an adjustment so that visual guide 410 is oriented on wire 416 at the wire-pull test location. Rather than automatically causing an adjustment to one or both of light emitting device movement mechanism 412 or table movement mechanism 414, the wire-pull test location logic may provide visual indicators 418 to a user of wire-pull environment 400 so that, if either or both of light emitting device 408 or table 404 upon which microelectronic package 402 rests cannot be adjusted automatically, the user may adjust a configuration of at least one of light emitting device 408 or table 402 so that visual guide 410 emitted by light emitting device 408 appears on wire 416 at the wire-pull test location as per an indication of the movement of the at least one of light emitting device 408 or table 402 to the user via visual indicators 418.

The above aspects and advantages of the illustrative embodiments of the present invention will be described in greater detail hereafter with reference to the accompanying figures. It should be appreciated that the figures are only intended to be illustrative of exemplary embodiments of the present invention. The present invention may encompass aspects, embodiments, and modifications to the depicted exemplary embodiments not explicitly shown in the figures but would be readily apparent to those of ordinary skill in the art in view of the present description of the illustrative embodiments.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system," Furthermore, aspects of the present invention may take the form of a computer program product embodied in any one or more computer readable medium(s) having computer usable program code embodied thereon.

Any combination of one or more computer readable medium(s) may be utilized. The computer readable medium may be a computer readable signal medium or a computer readable storage medium. A computer readable storage medium is a system, apparatus, or device of an electronic, magnetic, optical, electromagnetic, or semiconductor nature, any suitable combination of the foregoing, or equivalents thereof. More specific examples (a non-exhaustive list) the computer readable storage medium would include the following: an electrical device having a storage capability, a portable computer diskette, a hard disk, a random access memory (RAM), a read-only memory (ROM), an erasable programmable read-only memory (EPROM or Flash memory), an optical fiber based device, a portable compact disc read-only memory (CDROM), an optical storage device, a magnetic storage device, or any suitable combination of the foregoing. In the context of this document, a computer readable storage medium is any tangible medium that can contain or store a program for use by, or in connection with, an instruction execution system, apparatus, or device.

In some illustrative embodiments, the computer readable medium is a non-transitory computer readable medium. A non-transitory computer readable medium is any medium that is not a disembodied signal or propagation wave, i.e. pure signal or propagation wave per se. A non-transitory computer readable medium may utilize signals and propagation waves, but is not the signal or propagation wave itself. Thus, for example, various forms of memory devices, and other types of systems, devices, or apparatus, that utilize signals in any way, such as, for example, to maintain their state, may be considered to be non-transitory computer readable media within the scope of the present description.

A computer readable signal medium, on the other hand, may include a propagated data signal with computer readable program code embodied therein, for example, in a baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device. Similarly, a computer readable storage medium is any computer readable medium that is not a computer readable signal medium.

Computer code embodied on a computer readable medium may be transmitted using any appropriate medium, including but not limited to wireless, wireline, optical fiber cable, radio frequency (RF), etc., or any suitable combination thereof.

Computer program code for carrying out operations for aspects of the present invention may be written in any combination of one or more programming languages, including an object oriented programming language such as Java™, Smalltalk™, C++, or the like, and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems and computer program products according to the illustrative embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions that implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus, or other devices to produce a computer implemented process such that the instructions which execute on the computer or other programmable apparatus provide processes for implementing the functions/acts specified in the flowchart and/or block diagram block or blocks.

Figure 5:
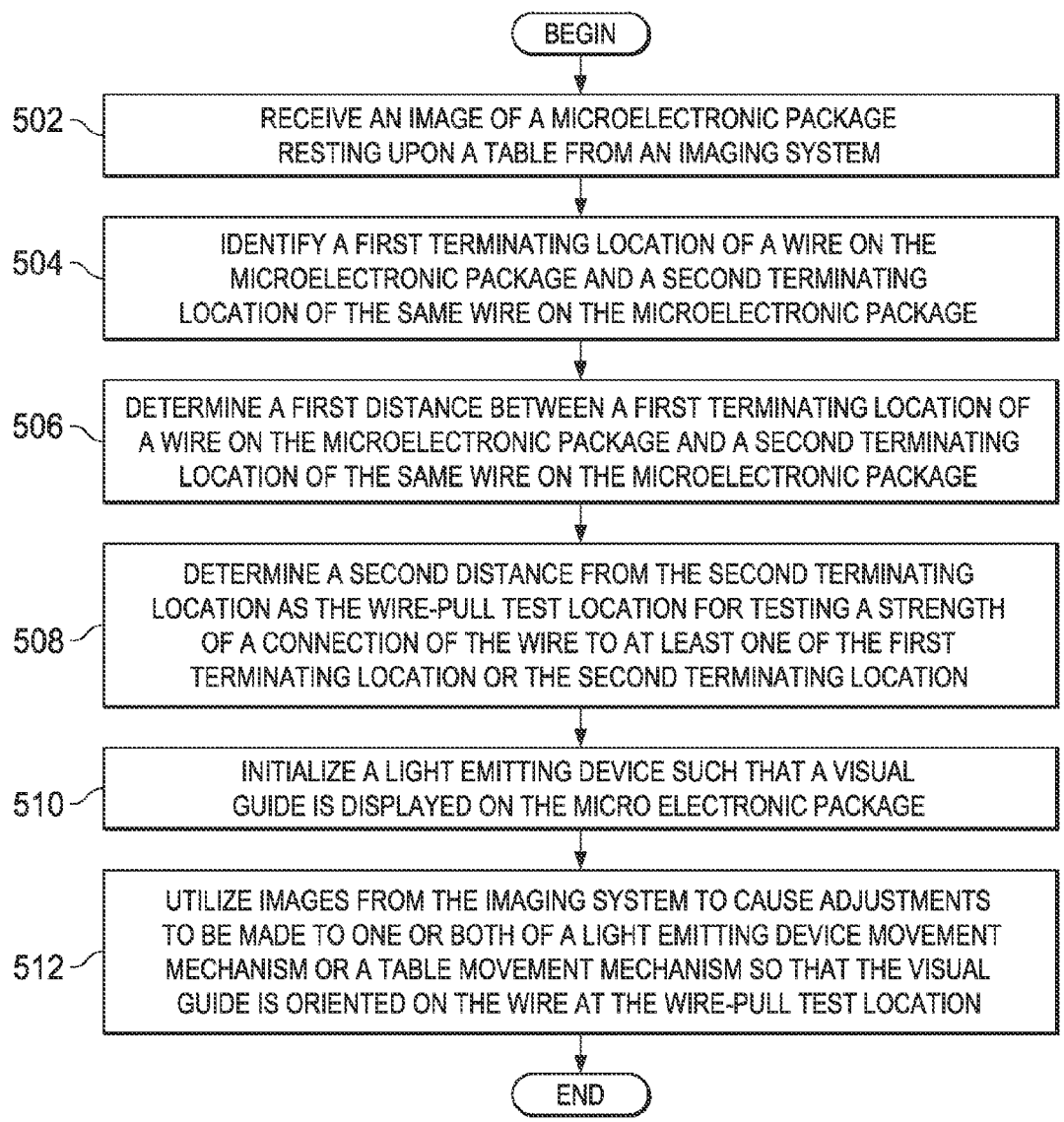
FIG. 5 depicts a flowchart of an operation performed by a wire-pull test location mechanism in accordance with an illustrative embodiment.

FIG. 5 depicts a flowchart of an operation performed by wire-pull test location mechanism in accordance with an illustrative embodiment. As the operation begins, the wire-pull test location mechanism receives an image of a microelectronic package resting upon a table from an imaging system (step 502). The wire-pull test location mechanism identifies a first terminating location of a wire on the microelectronic package and a second terminating location of the same wire on the microelectronic package (step 504). The wire-pull test location mechanism then determines a first distance between a first terminating location of a wire on the microelectronic package and a second terminating location of the same wire on the microelectronic package (step 506). Based on the first distance, the wire-pull test location mechanism determines a second distance from either the first terminating location or the second terminating location as the wire-pull test location for testing a strength of a connection of the wire to at least one of the first terminating location or the second terminating location (step 508).

With the wire-pull test location identified, the wire-pull test location mechanism initializes a light emitting device such that a visual guide is displayed on the microelectronic package (step 510). The wire-pull test location mechanism utilizes images from the imaging system to cause adjustments to be made to one or both of a light emitting device movement mechanism or a table movement mechanism, such that one or both of the light emitting device movement mechanism or the table movement mechanism are adjusted so that the visual guide is oriented on the wire at the wire-pull test location (step 512), with the operation ending thereafter. Although the flowchart is depicted for identifying a wire-pull test location on one wire of the microelectronic package, one or ordinary skill in the art will recognize that the operation executed by the wire-pull test location mechanism may be performed for each wire in the microelectronic package.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the Hock diagrams and/or flowchart illustration, can be implemented by special purpose hardware-based systems that perform the specified functions or acts, or combinations of special purpose hardware and computer instructions.

Thus, the illustrative embodiments provide mechanisms for identifying a wire-pull test location on a wire of a microelectronic package by projecting a visual guide at an optimal wire-pull test location on the microelectronic package. Utilizing the visual guide reduces need to estimate the location of the wire-pull. Further, by utilizing the visual guide, more accurate and precise measurements will be obtained for the wire-pull thus indicating whether the wire-bond interconnect is stable or good.

As noted above, it should be appreciated that the illustrative embodiments may take the form of an entirety hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

What is claimed is:

1. A method, in a data processing system, for identifying a wire-pull test location on a wire of a microelectronic package, the method comprising:
   determining a first distance between a first terminating location of the wire on the microelectronic package and a second terminating location of the wire on the microelectronic package;
   based on the first distance, determining a second distance from either the first terminating location or the second terminating location as the wire-pull test location for testing a strength of a connection of the wire to at least one of the first terminating location or the second terminating location; and
   performing an adjustment such that a visual guide is oriented on the wire at the wire-pull test location.

2. The method of claim 1, wherein the wire-pull test location is a predetermined distance, measured from either the first terminating location or the second terminating location.

3. The method of claim 1, wherein performing the adjustment comprises:
   adjusting a configuration of a light emitting device providing the visual guide, wherein the microelectronic package is in a fixed position and the light emitting device is automatically moved so that the visual guide appears on the wire at the wire-pull test location.

4. The method of claim 1, wherein performing the adjustment comprises:
   adjusting a configuration of a table upon which the microelectronic package rests, wherein a light emitting device providing the visual guide is in a fixed position relative to the table and the adjustment of the table comprises automatically moving the table so that the visual guide emitted by the light emitting device appears on the wire at the wire-pull test location.

5. The method of claim 1, wherein performing the adjustment comprises:
   adjusting a configuration of a light emitting device providing the visual guide and a configuration of a table upon which the microelectronic package rests, wherein the light emitting device and the table are automatically moved so that the visual guide emitted by the light emitting device appears on the wire at the wire-pull test location.

6. The method of claim 1, wherein performing the adjustment comprises:
   adjusting a configuration of at least one of a light emitting device or a table upon which the microelectronic package rests, wherein the at least one of the light emitting device or the table are manually moved by a user so that the visual guide emitted by the light emitting device appears on the wire at the wire-pull test location as per an indication of the movement of the at least one of the light emitting device or the table to the user.

7. The method of claim 1, wherein the visual guide is a reflection by the wire of a beam of light that is emitted from a light emitting device.

8. The method of claim 7, wherein the light emitting device comprises one of a light emitting diode (LED), a light bulb, or a laser.

9. The method of claim 7, wherein the light emitting device that is at an angle other than perpendicular to the microelectronic package so that the beam of light is reflected by the wire at the wire-pull test location without being blocked by a user performing a wire-pull test at the wire-pull test location.

10. The method of claim 7, wherein the light emitting device that is at a perpendicular angle to the microelectronic package so that the beam of light is reflected by the wire at the wire-pull test location without being blocked by a user performing a wire-pull test at the wire-pull test location.

11. The method of claim 1, wherein determining the first distance between the first terminating location of the wire on the microelectronic package and the second terminating location of the wire on the microelectronic package is performed via a digital imaging system.

12. The method of claim 1, wherein determining the first distance between the first terminating location of the wire on the microelectronic package and the second terminating location of the wire on the microelectronic package is performed via an optical imaging system through a scope.

13. The method of claim 1, wherein the microelectronic package comprises a plurality of components fixed to a substrate and wherein a first subset of the plurality of components are coupled to a second subset of the plurality of components via a set of terminators and a set of wires.

* * * * *